United States Patent [19]

Frank et al.

[11] Patent Number: 4,909,243
[45] Date of Patent: Mar. 20, 1990

[54] WOUND DRESSING SYSTEM

[75] Inventors: Margaret A. Frank; Frank M. Freeman, both of Lawrenceville, N.J.; George Cherry, Oxford, England

[73] Assignee: E. R. Squibb & Sons, Inc., Princeton, N.J.

[21] Appl. No.: 221,698

[22] Filed: Jul. 20, 1988

[51] Int. Cl.⁴ .............................................. A61L 15/00
[52] U.S. Cl. .................................. 128/156; 128/155; 128/165; 604/304
[58] Field of Search ....................... 128/155, 156, 165; 604/304

[56] References Cited

U.S. PATENT DOCUMENTS

| | | |
|---|---|---|
| 2,273,873 | 2/1942 | Klein . |
| 3,339,546 | 9/1967 | Chen . |
| 4,092,290 | 5/1975 | Bowser .......................... 524/443 |
| 4,393,080 | 7/1983 | Pawelchak et al. . |
| 4,393,150 | 5/1982 | Kresner .......................... 523/111 |
| 4,425,130 | 1/1984 | DesMarais ...................... 604/389 |
| 4,538,603 | 9/1985 | Pawelchak et al. . |
| 4,551,490 | 11/1985 | Doyle et al. . |
| 4,635,624 | 1/1987 | Gilman . |
| 4,753,232 | 6/1988 | Ward ............................. 128/156 |

FOREIGN PATENT DOCUMENTS 2150028 11/1983 United Kingdom ................ 128/156

OTHER PUBLICATIONS

Dent, A., Weeono, L., "Caring for Leg Ulcers", Nursing Mirror, 1985, No. 25.

Primary Examiner—Richard J. Apley
Assistant Examiner—N. Paul
Attorney, Agent, or Firm—Theodore R. Furman, Jr.

[57] ABSTRACT

A novel two-piece wound dressing, providing protection during dressing changes to the delicate healing skin directly surrounding the wound, is provided according to the present invention. The dressing comprises a baseplate having an adhesive surface for contacting surrounding skin, and has an aperture extending completely through it over which a wound pad of a desired wound dressing material can be placed. Means are also provided for attaching the wound pad to the baseplate.

19 Claims, 2 Drawing Sheets

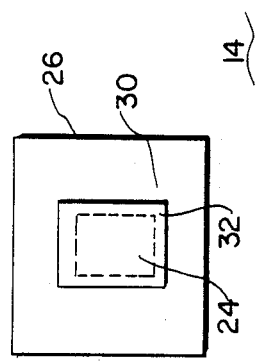
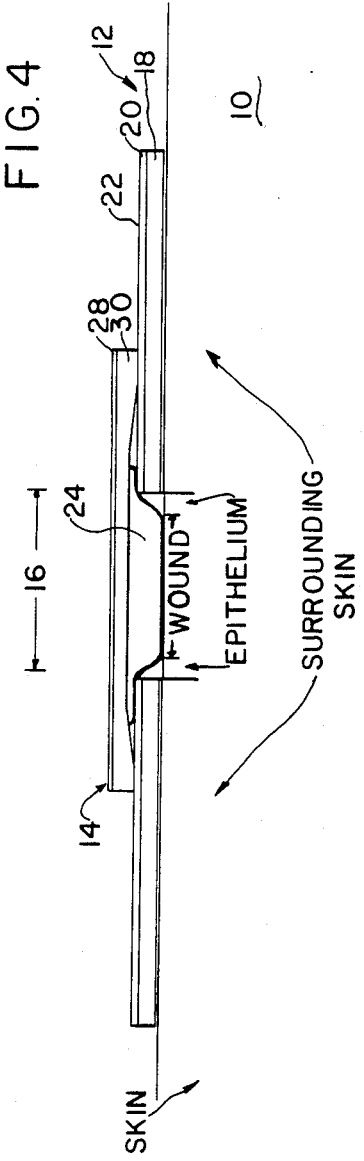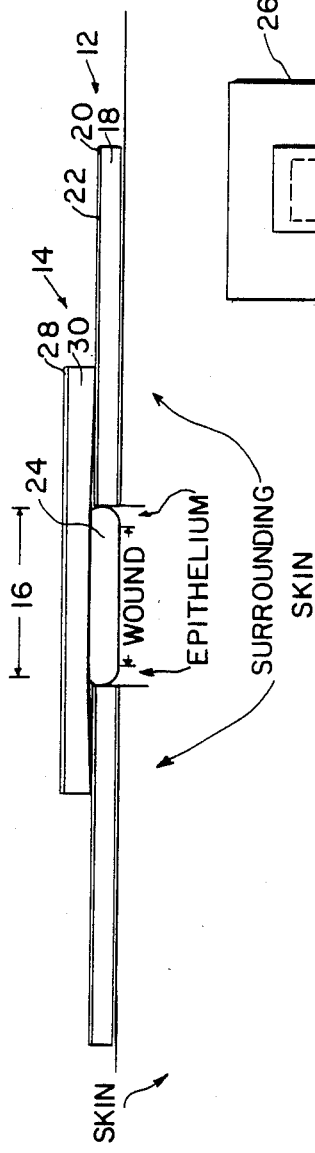

WOUND DRESSING SYSTEM

FIELD OF THE INVENTION

The present invention relates to a dressing system useful for the treatment of wounds and particularly concerns a dressing especially suitable for leg ulcers.

BACKGROUND OF THE INVENTION

In the area of wound care, which is understood to include burns, pressure sores, ulcers and the like, it is typical to focus the choice/design of dressings or medicaments on the specific requirements of the wound itself. The most complete and effective wound care, however, concerns itself additionally with the needs of:

(1) the epithelium, which is the tender area of new cell growth directly peripheral to the wound; and, (2) the surrounding non-wounded skin. Indeed, many dermatologists feel that care of the epithelium and surrounding skin is paramount in the successful treatment of wounds, such as leg ulcers. Since the epithelium is the area in which the actual healing occurs (i.e., it is generally accepted that healing of a wound occurs by cell growth from the periphery inward), great care should be taken not to damage this area. Problems occur during dressing changes when either the dressing adheres to this area or when the new cell growth becomes entwined within the matrix of the dressing. Injury to the epithelium during dressing changes can effectively negate the care provided to the wound.

The non-wounded skin beyond the epithelium is usually in contact with some portion of the wound dressing system which maintains the dressing positioned on the wound. For example, the surrounding skin may be covered for extended periods with a wrap and/or adhesive to hold the dressing in place. Many such dressings can irritate this surrounding skin and compound the problem to the patient. This is especially true in the area of leg ulcers wherein the surrounding skin can easily become sensitized by strong medicaments and is often plagued with flaking, scaling and eczema.

The time frame for the changing of dressings depends on the above concerns and therefore opinions as to how often dressings should be changed vary drastically. It may be highly desirable to change dressings often in certain cases where the wound is emitting a large volume of exudate. Also, considering the various types of dressings available and the various stages in the healing process, dressings should ideally be altered to optimally treat the then-present condition of the wound.

In the area of leg ulcers one type of treatment presently used comprises the application of gauze to the ulcer and the utilization of a compression wrap to secure the gauze to the ulcer. Since the gauze quickly becomes saturated, frequent changes are necessary and damage to the epithelium and surrounding skin may occur. If the gauze is left on for too long a period, the exudate which contains proteolytic enzymes can begin to digest the patient's surrounding skin.

A second type of treatment is the Unna's Boot (commercially available from Biersdorf, Inc.) which comprises a zinc paste-containing bandage wrapped around the patient's leg from above the toes to below the knee. Other Unna's Boot/zinc impregnated treatments are available from Miles and Graham Field. This dressing is typically left in place for a week at a time and absorbent pads must be applied to the outside of the dressing in the area of the ulcer to absorb excess exudate. Seepage of exudate throughout the wrap is common, however, and damage to the skin and epithelium is inevitable.

A wound dressing system which could facilitate frequent dressing changes, while protecting the epithelium and surrounding non-wounded skin, would be a useful addition to the wound care art.

SUMMARY OF THE INVENTION

In accordance with the present invention a two-piece wound dressing system facilitating frequent dressing changes and protection of the delicate surrounding skin is disclosed. The wound dressing system comprises an adhesive baseplate which covers the surrounding skin and which has an aperture through which the wound is exposed. A wound pad, having a dressing element of a known wound dressing material, is placed over the aperture and releaseably adhesive means are provided to keep the wound pad in contact with the wound.

BRIEF DESCRIPTION OF THE DRAWING

FIG. 2 is a view of the wound contacting surface of a wound pad of the present system.

FIGS. 3, 4 and 5 illustrate the wound dressing systems of the present invention shown cross-sectionally in the relationship with the wound area.

DETAILED DESCRIPTION OF THE INVENTION

As mentioned above, the wound dressing of the present invention provides more versatile wound care in that dressing changes can be made as often as required without the fear of damaging the delicate healing skin peripheral to the wound. This is possible because the baseplate can be left in place on the surrounding healthy skin for extended periods of time. The wound pad is maintained in place over the wound by whatever means are employed to attach the pad to the baseplate. Means for attaching the pad to the baseplate should be releaseable and optionally resealable so that a first pad can be removed and a second can be sealed in its place on the baseplate.

Thus, the wound dressing of the present invention provides more complete care to the wound area, especially in the care of leg ulcers, in that a more versatile treatment can be given to the wound itself while ensuring protection to the surrounding area.

Figure 1:
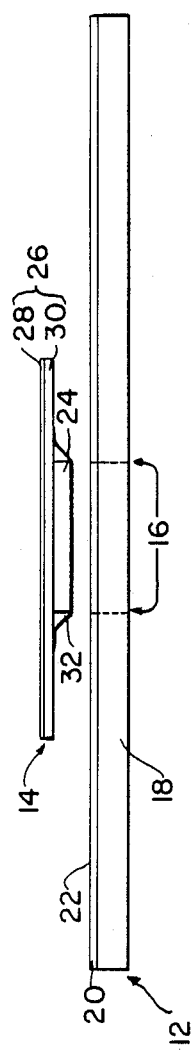
FIG. 1 is a cross-sectional view of a wound dressing system of the present invention.

Referring to FIG. 1, an embodiment of the wound dressing 10 of the present invention is shown to have a baseplate 12 and a wound pad 14 which is designed to fit over, or optionally into, the aperture 16 which extends through the baseplate 12 and which corresponds generally to the size and shape of a wound (not shown). The baseplate 12 comprises a first adhesive layer 18 which is designed to contact the skin and a first backing layer 20 which overlies the first adhesive layer 18. The wound pad 14 must be able to be releaseably and optionally resealably adhered to the upper surface 22 of the first backing layer 20 of the baseplate 12.

The wound pad 14 comprises a dressing element 24 adhered to a top layer 26 which, in turn, comprises a second backing layer 28 and optionally a second adhesive layer 30. The second adhesive layer 30 can serve as the releaseable, resealable adhesive means and must be able to release from the upper surface 22 of the baseplate 12 substantially more easily than the first adhesive layer 18 releases from the skin of the patient. If the optional second adhesive layer 30 is not present, alternate means known in the art for releaseably adhering the wound pad 14 to the baseplate 12 should be provided.

The dressing element 24 of the wound pad 14 may be enveloped by an overwrap (not shown) which contains the dressing element 24 and maintains its integrity during use. The wound pad 14 may further include a nonadherent material 32 which covers the surface of the dressing element 24 which ultimately contacts the wound.

FIG. 2 more clearly illustrates a typical relationship among the elements of the wound pad 14 (viewed from the side which contacts the wound), i.e. the top layer 26, dressing element 24 adhered thereto, and the optional second adhesive layer 30 and optional nonadherent material 32.

The first adhesive layer 18 of the baseplate 12 of the present dressing comprises a plate (which can be thin in the form of a sheet) of a pliable adhesive material. Fluid-interactive adhesives known in the art for the treatment of wounds which emit exudate are preferred and they typically comprise hydrocolloids dispersed in a polymer matrix. Also, the adhesive material for the baseplate is preferably capable of adhering to moist surfaces. Adhesive compositions known in the art for use in ostomy skin barriers and male incontinence applications are especially well-suited for the baseplate of the present invention.

For example, Chen in U.S. Pat. No. 3,339,545 discloses an adhesive comprising a blend of one or more water soluble or water swellable hydrocolloids and a viscous substance such as polyisobutylene. A film of water insoluble material, corresponding to the backing layer in the instant case, is affixed to one surface of the adhesive. This article is commercially available as Stomahesive TM from E. R. Squibb and Sons, Inc.

Doyle et al. in U.S. Pat. No. 4,551,490 disclose a pressure sensitive adhesive suitable for medical purposes comprising 5 to 30 percent by weight of one or more polyisobutylenes or a blend of one or more polyisobutylenes and butyl rubber, 3 to 20 percent by weight of one or more styrene radial or block type copolymers, 8 to 40 percent by weight of mineral oil, 15 to 65 percent by weight of one or more water soluble hydrocolloid gums, up to 15 percent by weight of one or more water swellable cohesive strengthening agents provided that the hydrocolloid gums and strengthening agents together are present in an amount of between about 15 and 65 percent by weight, and 7.5 to 15 percent by weight of a tackifier.

Pawelchak et al., in U.S. Pat. No. 4,393,080 discloses an adhesive composition comprising 30 to 70 percent by weight of a pressure sensitive viscous adhesive material and an optional thermoplastic elastomer. The pressure sensitive material is selected from natural rubber, silicone rubber, acrylonitrile rubber, polyurethane rubber and polyisobutylenes. The elastomer can be medium molecular weight polyisobutylene, butyl rubber or styrene copolymers. This adhesive material further includes 3 to 60 percent by weight of material or synthetic polymers capable of developing elastomeric properties when hydrated which can be gluten and long chain polymers of methyl vinyl ether/maleic acid.

While the above adhesives are well suited for use in the baseplate 12 of the present invention, they are merely meant to be exemplary and any skin compatible adhesive could be employed, with the fluid interactive adhesives preferred.

In a preferred embodiment the adhesive material of the baseplate 12 further includes between 2 and 20 percent and preferably about 10 percent by weight of zinc oxide. The zinc oxide not only aids in the care of the skin surrounding the wound, but surprisingly the fluid interactive adhesive materials become more pliable with the zinc oxide included.

The first backing layer 10 of the baseplate 12 can be of any polymer film, nonwoven material, weave or the like, or combination thereof, known in the art, with flexible polyurethanes and embossed polyethylene films preferred.

The dressing element 24 of the wound pad 14 can also be of any convenient material or materials used as wound dressings in the wound care art. Typical materials include, but are not limited to, natural and synthetic polymeric absorbents, hydrocolloid/polysaccharide absorbents, cellulosic absorbents, gum and resin absorbents, inorganic absorbents, gel-forming fluid-interactive adhesive dressings, wool, cotton, lint and superabsorbents, i.e. water swellable polymers typically in the form of fiber or flock material. The structure of the dressing element 24 may comprise a complete laminated dressing, e.g. that described by Pawelchak et al. in U.S. Pat. 4,538,603 wherein an occlusive dressing commercially available from E. R. Squibb & Sons, Inc. as Duoderm TM is disclosed. Pawelchak et al. describe dressings comprising an adhesive layer of a gel-forming fluid interactive adhesive, a layer of semi-open cell polymeric foam and a polymeric film backing layer. The dressing may also include a second adhesive layer designed to enhance cohesion. Also, a copending application U.S. Ser. No. 931,501 entitled "ADHESIVE STRUCTURE AND PRODUCTS INCLUDING SAME" filed Nov. 17, 1986 now U.S. Pat. No. 4,793,337, describes a dressing similar to the double adhesive structure of Pawelchak but which also includes a layer of calcium alginate wool or fiber interposed the adhesive layer. Any other pad, gauze or wound film known in the art, e.g., materials from the diaper and incontinence arts, can be utilized as the dressing element 24. Specific suitable dressings include Sunbeam Process absorbent materials (Gelman Technology), the Composite Air Laid Superabsorbent Pad (Dry Forming Processes) and Polysteen Superabsorbent Fiber Flock SAFF (Hanfspinnerei Steen & Co.)

These and various other wound dressings are suitable for use as the dressing element 24 in the wound pad 14 of the wound dressing of the present invention. Regardless of the material chosen, the dressing element 24 should be capable of handling the wound fluids so as to protect the wound and surrounding areas from the deleterious effects thereof. This is accomplished by the dressing element's ability to remove or "wick" the fluids away from the wound.

The second backing layer 28 can be chosen from the same materials as the first backing layer 20 and can be the same as, or different than, the first backing layer 20. A preferred second backing layer is a spun laced polyester nonwoven (e.g., Kendall's Novenette) bonded to a polyester film.

As mentioned above, when the dressing element 24 is a gauze or composite pad, it may further include an overwrap, e.g. a polyester nonwoven overwrap (e.g., those available from Kendall, Fasson, Semex and the like) and a non-adherent facing as is known in the art.

The second adhesive layer 30, if employed, can be of any convenient adhesive that can release easily from the first backing layer 20. In one embodiment, the adhesive for this layer should also be resealable in the event that the wound pad 14 is not to be changed, but just put back in place after examination of the wound.

Figure 3:
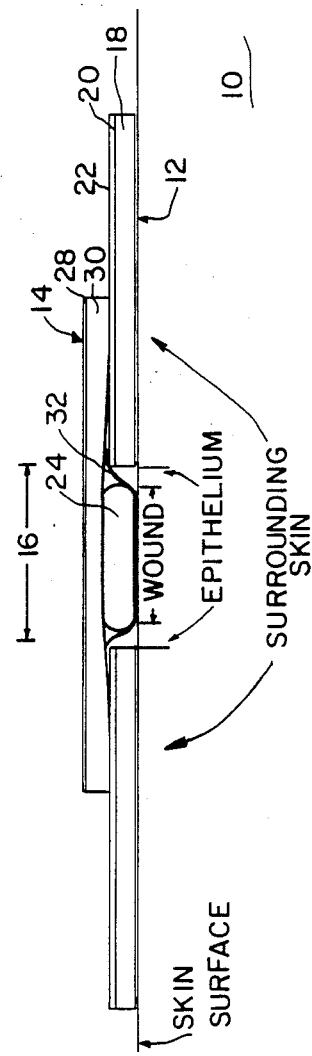

FIGS. 3, 4 and 5 show structurally some of the embodiments of the present invention in contact with a wound. In FIG. 3 the dressing element 24 is shown to be about the same size as the wound. The aperture 16 has been cut to be about the same size as the wound plus the epithelium. The dressing element 24 draws wound exudate away from the wound and keeps it away from the epithelium. The non-adherent material 32 not only prevents the dressing element 24 from sticking to the wound, but also presents any adherence to the epithelium.

In FIG. 4, the dressing element 24 is designed larger than the wound and aperture 16. The materials of the wound pad 14 are typically thin and flexible enough to bend into the aperture 16. When swellable materials are employed in the dressing element 24, the material swells into a self-forming "plug".

FIG. 5 shows a designed "plug" structure for the dressing element 24 wherein the material is of the element 24 is nearly exactly the same size and shape as the aperture 16. This arrangement is well suited when the gel forming wound dressings, e.g. Duoderm, are used as the dressing element 24. The aperture 16 in any of FIGS. 3, 4 or 5 could be made to expose only the wound and not the wound and the epithelium. However, this choice should be made by the caregiver and depends on the condition of the wound and the materials chosen for the wound dressing of the invention.

In a preferred embodiment the baseplate comprises a first adhesive layer, bonded to an embossed polyethylene film. The first adhesive layer is of a pressure sensitive adhesive like those described above by Doyle et al. in U. S. Pat. No. 4,551,490 (e.g. Durahesive TM from E. R. Squibb & Sons, Inc.) further including 10 percent by weight of zinc oxide. The adhesive layer is typically 15-20 mils thick but could be of any convenient thickness.

The wound pad in a preferred embodiment comprises a Composite Air Laid Superabsorbent Pad (commercially available from Dry Forming Processes) as the dressing element enveloped in a polyester nonwoven overwrap and having its wound contact surface covered by Delnet P530N fabric facing. The dressing element is adhered to the top layer which consists of Kendall Novenette (spun laced polyester nonwoven bonded to a 0.0005" thick polyester film) and I679 Acrylic Copolymer Adhesive (commercially available from Avery).

In practice an aperture of desired shape and size is cut through the baseplate. The baseplate is then adhered to the body surface so that the aperture aligns with the wound. The wound pad is placed over the aperture and can be removed/replaced/ changed as is necessary while leaving the baseplate in place on the body for extended periods (i.e., a week or more).

This system is especially well suited for the care of leg ulcers in that the baseplate can comprise a large sheet of material which can be tightly and securely placed around the leg in one operation without the need for a spiral overwrap process as in the prior art. Various dressing changes can be made throughout the course of a week while protecting the surrounding skin. In the care of leg ulcers, a compression bandage can be used in conjunction with the present system.

Since the wound dressing system of the present invention is made of various materials, adhesives, etc. known in the art, it is understood that one skilled in the wound care art could manufacture this two-piece system by well-established techniques.

What is claimed is:

1. A wound dressing system for use in the care of a wound and the surrounding area comprising
    a substantially flat, pliable baseplate comprising a first major surface being a first adhesive surface capable of maintaining said dressing in contact with a wound wherein said first adhesive surface comprises a fluid interactive adhesive comprising hydrocolloids dispersed in a polymer matrix and further comprising 2 to 20 percent by weight of zinc oxide site; and, a second major surface being a first backing layer, opposed to said first major surface, and to which a wound pad can be releaseably contacted; further wherein said baseplate includes an aperture extending therethrough from said first major surface to said second major surface, which aperture corresponds substantially in shape and size to said wound;
    a wound pad comprising a dressing element of a material capable of accommodating exudate emitted from said wound and promoting healing of said wound, bonded to a second backing layer overlying said dressing element, wherein a surface of said dressing element which is to contact the wound is at least of the same dimensions as said wound, and which is positioned over said aperture such that said dressing element substantially covers said wound; and,
    releaseable adhesive means for holding said wound pad to said baseplate and thereby over said wound.

2. The system of claim 1 wherein said second backing layer on said wound pad is larger than the dimensions of said aperture and further wherein said releaseable adhesive means for holding said wound pad in place comprises a second adhesive layer of a releaseable adhesive material on that portion of said second backing layer which overlaps said aperture to provide releaseable adhesion of said wound pad to said baseplate.

3. The system of claim 2 wherein said second adhesive layer is also resealable to the first backing layer of the baseplate.

4. The system of claim 1 wherein said first adhesive layer comprises 5 to 30 percent by weight of one or more polyisobutylenes or a blend of one or more polyisobutylenes and butyl rubber, 3 to 20 percent by weight of one or more styrene radial or block type copolymers, 8 to 40 percent by weight of mineral oil, 15 to 65 percent by weight of one or more water soluble hydrocolloid gums, up to 15 percent by weight of one or more water swellable cohesive strengthening agents provided that the hydrocolloid gums and strengthening agents together are present in an amount of between about 15 and 65 percent by weight, and 7.5 to 15 percent by weight of a tackifier and between about 2 and 20 percent by weight of zinc oxide.

5. The system of claim 1 wherein said first adhesive layer includes 10 percent by weight of zinc oxide.

6. The system of claim 1 wherein said first and second backing layers are selected from polymer films, nonwoven materials, woven materials or combinations thereof.

7. The system of claim 1 wherein said first backing layer is selected from flexible polyurethane and embossed polyethylene films.

8. The system of claim 1 wherein said second backing layer is a spun laced polyester nonwoven material bonded to a polyester film.

9. The system of claim 1 wherein said dressing element is a pad, gauze, dressing or film of a material or materials selected from natural and synthetic polymeric absorbents, hydrocolloid/polysaccharide absorbents cellulosic absorbents, gum and resin absorbents, inorganic absorbents, gel-forming fluid-interactive adhesive dressings, wool, cotton, lint and superabsorbents.

10. The system of claim 9 wherein said dressing element further comprises a polyester overwrap.

11. The system of claim 9 wherein said dressing element further comprises a non-adherent material on its wound-contacting surface.

12. The system of claim 1 wherein said aperture is sufficiently large to expose said wound and an epithelium peripheral to said wound.

13. The system of claim 1 wherein said dressing element is smaller than said aperture.

14. The system of claim 1 wherein said dressing element is larger than said aperture.

15. The system of claim 1 wherein said dressing element has substantially the same dimensions as said aperture.

16. A method of treating wounds which provides for frequent changes of wound dressings while protecting the wound epithelium and surrounding skin, which method comprises employing the wound dressing system of claim 1.

17. A method of treating leg ulcers which provides for frequent changes of dressings while protecting the epithelium and surrounding skin, which method comprises employing the wound dressing system of claim 1.

18. The system of claim 1 wherein said baseplate is of dimensions sufficient to cover a substantially greater area than the wound area covered by said wound pad.

19. The method of claim 17 wherein said baseplate covers a substantial area of the leg surrounding the leg ulcer to be treated.

* * * * *